(12) United States Patent
Stewart

(10) Patent No.: US 8,961,486 B2
(45) Date of Patent: Feb. 24, 2015

(54) ABSORBENT ARTICLE

(76) Inventor: Vesna Stewart, Winter Haven, FL (US)

(*) Notice: Subject to any disclaimer, the term of this patent is extended or adjusted under 35 U.S.C. 154(b) by 260 days.

(21) Appl. No.: 13/556,194

(22) Filed: Jul. 23, 2012

(65) Prior Publication Data

US 2014/0025028 A1 Jan. 23, 2014

(51) Int. Cl.
*A61F 13/15* (2006.01)

(52) U.S. Cl.
USPC ..................................... 604/385.17

(58) Field of Classification Search
CPC ............... A61F 13/47218; A61F 13/47227; A61F 13/47272; A61F 213/1513; A61F 213/4706; A61F 213/4729
USPC ....................... 604/385.17, 385.18
See application file for complete search history.

(56) References Cited

U.S. PATENT DOCUMENTS

| | | | | |
|---|---|---|---|---|
| 4,533,357 A | * | 8/1985 | Hall | 604/401 |
| 5,743,896 A | * | 4/1998 | Parker | 604/385.01 |
| 6,652,503 B1 | * | 11/2003 | Bradley | 604/385.17 |
| 7,594,905 B2 | * | 9/2009 | Tanio et al. | 604/385.27 |
| 8,147,471 B2 | * | 4/2012 | Roche del Ayala | 604/385.17 |
| 8,523,833 B2 | * | 9/2013 | Springman | 604/385.01 |
| 2008/0172018 A1 | * | 7/2008 | Chien | 604/385.04 |
| 2008/0172019 A1 | * | 7/2008 | Chien | 604/385.04 |
| 2009/0088716 A1 | * | 4/2009 | Nwokeji | 604/385.04 |

* cited by examiner

*Primary Examiner* — Lynne Anderson
(74) *Attorney, Agent, or Firm* — Cygnet IP Law, P.A.; Stephen W. Aycock, II

(57) ABSTRACT

An absorbent pad is described. The absorbent pad can include a main body having a top absorbent surface and an intergluteal extension formed perpendicular to the top absorbent surface of the main body portion, the intergluteal extension disposed near one side of the main body portion and having a triangular shape with an angle from a center portion of the main body portion extending to an outer edge of the main body portion.

5 Claims, 6 Drawing Sheets

ABSORBENT ARTICLE

Embodiments relate generally to disposable absorbent articles and more particularly to disposable absorbent articles having an intergluteal extension.

BACKGROUND

For convenience, discreetness and protection, women who are menstruating or who have light incontinence issues may wear a disposable absorbent article such as a pantiliner or a sanitary napkin. A person wearing an absorbent article while laying down for a period of time may experience a leakage of fluid toward the backside along the intergluteal cleft.

Conventional feminine pads, pantiliner and sanitary napkins often have a generally flat absorbent surface and may not be configured to intercept a flow of fluid escaping along the intergluteal cleft.

Embodiments were conceived in light of the above-mentioned problems or limitations, among other things.

SUMMARY

An embodiment includes an absorbent pad having a main body with a first lateral edge, a second lateral edge, a first longitudinal edge, a second longitudinal edge, a longitudinal width extending from the first lateral edge to the second lateral edge, and a lateral width extending from the first longitudinal edge to the second longitudinal edge. The main body portion can comprise a liquid pervious top sheet, a liquid impervious back sheet, and an absorbent system disposed between the top sheet and the back sheet. The main body portion can also include an adhesive element disposed on an exterior surface of the back sheet. The absorbent pad can also include an intergluteal extension portion disposed perpendicular to a surface of the main body portion.

Another embodiment can include an absorbent pad having a main body portion that conforms to the contours of a woman's pudendal region. The absorbent pad can also include an intergluteal extension coupled to the main body portion via an absorbent cord.

Another embodiment includes an absorbent article having a main body portion with an intergluteal extension formed perpendicular to a surface of the main body portion. The intergluteal extension having a series of accordion folds between a top edge of the intergluteal extension and an edge of the intergluteal extension connecting to the main body portion.

Another embodiment can include an incontinence pad having a main body portion and an intergluteal extension portion disposed near one end of the main body portion and formed so as to be perpendicular to a surface of the main body portion.

Yet another embodiment includes a training pant or diaper for infants or children, the training pant or diaper having a main body portion and an intergluteal extension formed near a back surface of the main body portion and formed perpendicular to a surface of the main body portion. The diaper can also include a fold disposed near a top edge on the back side of the diaper and folded inward so as to help prevent leakage of bodily fluids from the top back edge of the diaper.

DETAILED DESCRIPTION

The present disclosure is directed to absorbent articles having an intergluteal extension. The intergluteal extension may be attached to a surface of the absorbent article near an edge that is disposed and adapted to be placed near the gluteus. In another embodiment, the intergluteal extension may be connected to the absorbent article via an absorbent cord.

The intergluteal extension is adapted to prevent fluid from escaping the absorbent article via the intergluteal cleft. For example, when a person is lying down and is experiencing menstruation or incontinence, the intergluteal extension can prevent fluids associated with either event from escaping and leaking via the intergluteal cleft.

Figure 1:
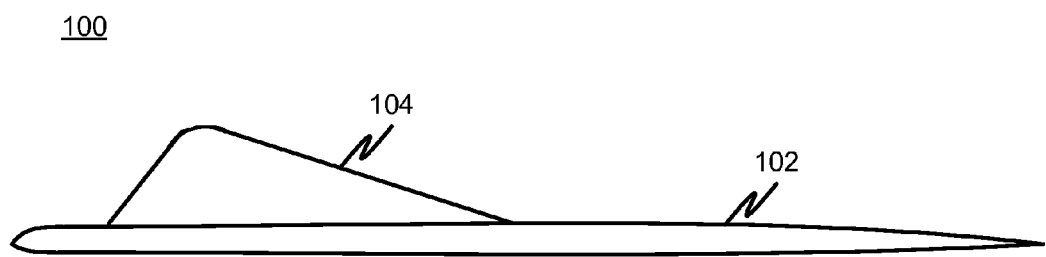
FIG. 1 is a side elevation view of an example absorbent article in accordance with at least one embodiment.
Figure 2:
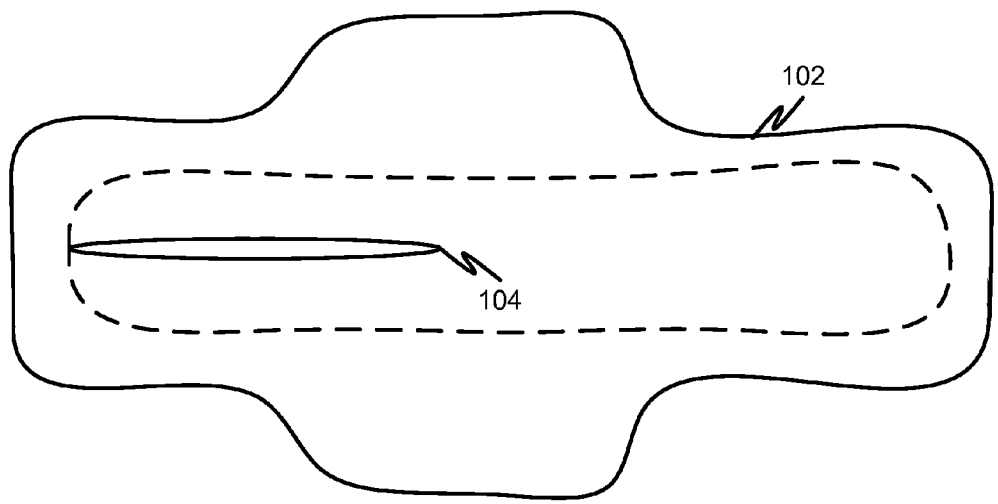
FIG. 2 is a top elevation view of an example absorbent article in accordance with at least one embodiment.

FIGS. 1 and 2 show an example absorbent article 100 (e.g., a feminine hygiene pad, pantiliner or sanitary napkin) having a main body portion 102 and an intergluteal extension 104. The main body portion 102 of the absorbent article can be formed so as to conform to the contours of a woman's pudendal region. The intergluteal extension 104 is formed generally perpendicular to a main absorbent surface of the main body portion. The intergluteal extension 104 is attached to the main body portion 102 and disposed near an edge of the main body portion to be placed adjacent to the intergluteal cleft. The intergluteal extension 104 slopes downward toward the interior of the main body portion 102.

The intergluteal extension 104 can be folded sideways to lay parallel to a surface of the main body portion 102 for packaging.

The absorbent article 100 (and any other embodiments described herein) can be formed in different sizes to suit the needs of a wearer and can be formed from any now know or later developed materials suitable for absorbent articles.

Figure 3:
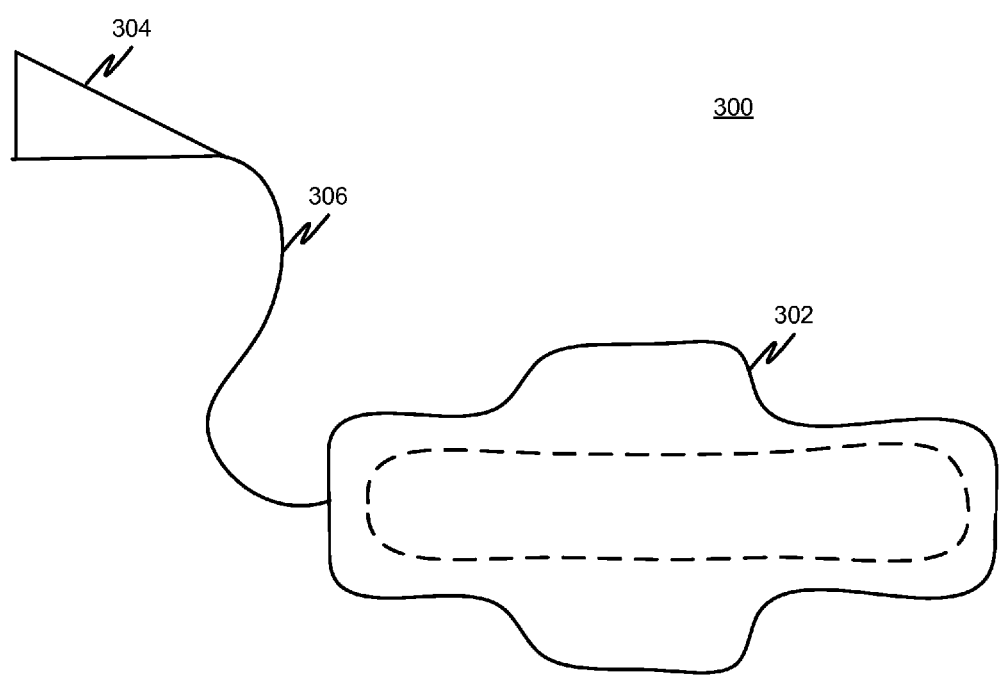
FIG. 3 is a top elevation view of an absorbent article having an intergluteal extension connected via an absorbent cord in accordance with at least one embodiment.

FIG. 3 shows an example absorbent article 300 having a main body portion 302, an intergluteal extension 304, and an absorbent cord 306 connecting the intergluteal extension 304 to the main body portion 302.

Having a movable intergluteal extension 304 as shown in FIG. 3 can allow the absorbent article to accommodate wearers of different body shapes and sizes.

Figure 4:
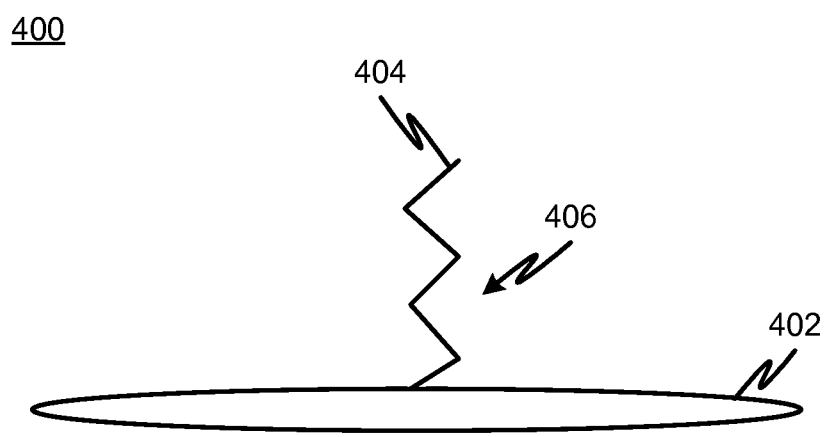
FIG. 4 is an end elevation view of an absorbent article having an intergluteal extension in accordance with at least one embodiment.
Figure 5:
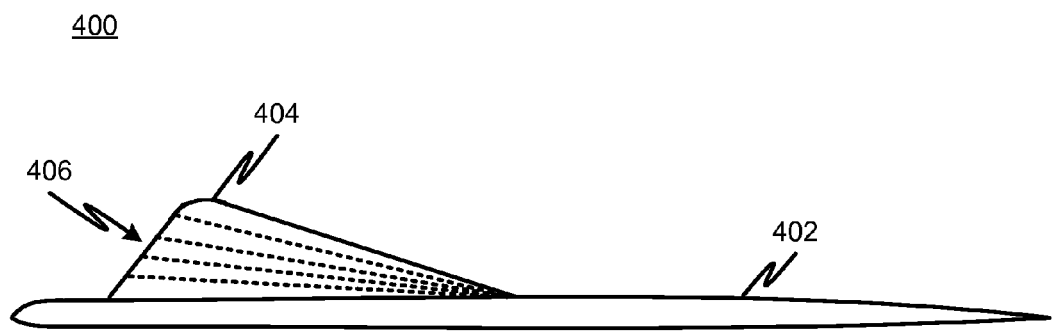
FIG. 5 is a side view of an absorbent article having an intergluteal extension with accordion folds in accordance with at least one embodiment.

FIGS. 4 and 5 show an example absorbent article 400 having a main body portion 402 and an intergluteal extension portion 404 with accordion folds 406. The accordion folds 406 can permit the intergluteal extension 404 to fold flat for packing, storage and/or shipping of the absorbent article 400.

Figure 6:
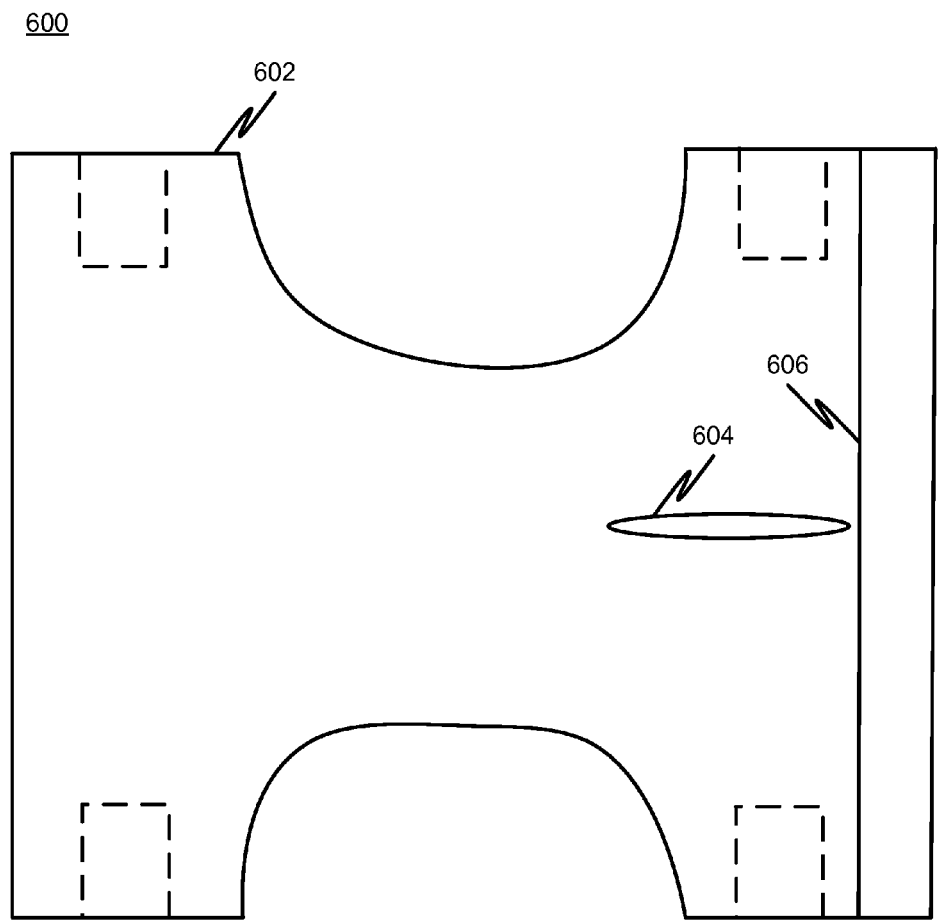
FIG. 6 is an example diaper having an intergluteal extension and a top edge fold in accordance with at least one embodiment.

FIG. 6 shows a baby diaper 600 having a main body portion 602 and intergluteal extension portion 604, a fold portion 606, and attachment portions 608 and 610. In use, the baby diaper 600 has an intergluteal extension portion 604 to help prevent bodily fluids or waste from exiting the diaper via the intergluteal cleft. In addition to, or as an alternative to, the intergluteal extension 604, the baby diaper 600 can include a fold along a top edge of the back side of the diaper. The fold 606 can also help prevent bodily fluids or waste from exiting the diaper from the rear.

It is therefore apparent that there is provided in accordance with the various embodiments disclosed herein, absorbent articles.

While the invention has been described in conjunction of a number of embodiments, it is evident that many alternatives, modifications and variations would be or are evident to those of ordinary skill in the applicable arts. Accordingly, Applicant intends to embrace all such alternatives, modifications, equivalent and variations that are within the spirit and scope of the invention.

What is claimed is:

1. An absorbent article comprising:
   a main body portion;
   an intergluteal extension portion; and
   an absorbent cord connecting one end of the intergluteal extension portion to a first edge of the main body portion.

2. The absorbent article of claim 1, wherein the main body portion includes a first lateral edge, a second lateral edge, and first longitudinal edge, a second longitudinal edge, a longitudinal width extending from the first lateral edge to the second lateral edge, and a lateral width extending from the first longitudinal edge to the second longitudinal edge.

3. The absorbent article of claim 1, wherein the main body portion includes a liquid pervious top sheet, a liquid impervious back sheet, and an absorbent system disposed between the top sheet and the back sheet.

4. The absorbent pad of claim 3, further comprising an adhesive element disposed on an exterior surface of the back sheet.

5. The absorbent pad of claim 1, wherein the intergluteal extension has an impervious top sheet and an absorbent system disposed underneath the impervious top sheet.

* * * * *